United States Patent [19]

Effland et al.

[11] Patent Number: 4,916,135
[45] Date of Patent: Apr. 10, 1990

[54] N-HETEROARYL-4-QUINOLINAMINES

[75] Inventors: Richard C. Effland; Joseph T. Klein, both of Bridgewater; Larry Davis, Sergeantsville; Gordon E. Olsen, Somerset, all of N.J.

[73] Assignee: Hoechst Roussel Pharmaceuticals Inc., Somerville, N.J.

[21] Appl. No.: 348,937

[22] Filed: May 8, 1989

[51] Int. Cl.[4] .................. A61K 31/495; C07D 401/12
[52] U.S. Cl. .................. 514/254; 514/232.8; 514/235.5; 514/297; 514/313; 544/126; 544/128; 544/361; 544/363; 546/106; 546/162
[58] Field of Search .............. 544/363, 361, 126, 128; 546/106, 162; 514/234, 232.8, 235.5, 297, 313

[56] References Cited

U.S. PATENT DOCUMENTS

| | | | |
|---|---|---|---|
| 3,232,945 | 2/1966 | Sigal et al. | 544/362 |
| 3,318,895 | 5/1967 | Pribyl et al. | 544/362 |
| 3,541,066 | 11/1970 | Wolf et al. | 260/398 |
| 3,580,915 | 5/1971 | Wolf et al. | 546/88 |
| 3,987,047 | 10/1976 | Grins et al. | 540/521 |
| 4,108,998 | 8/1978 | Demerson et al. | 544/361 |
| 4,575,553 | 3/1986 | Kavadias et al. | 546/106 |
| 4,631,286 | 12/1986 | Shuske et al. | 514/297 |
| 4,695,573 | 9/1987 | Shuske et al. | 514/290 |
| 4,743,601 | 5/1988 | Schonafinger et al. | 514/229.8 |
| 4,752,610 | 6/1988 | Effland et al. | 514/343 |
| 4,753,950 | 1/1988 | Shutske et al. | 514/291 |
| 4,762,481 | 8/1988 | Shutske et al. | 514/278 |
| 4,789,678 | 12/1988 | Effland et al. | 514/313 |
| 4,792,562 | 12/1988 | Effland et al. | 514/343 |
| 4,800,203 | 1/1989 | Hamer et al. | 514/248 |
| 4,806,554 | 2/1989 | Effland et al. | 514/338 |

FOREIGN PATENT DOCUMENTS 0268871 6/1988 European Pat. Off. .
1022940 3/1966 United Kingdom .

OTHER PUBLICATIONS

Patnaik et al., "J. Med. Chem.", vol. 9, 1966, pp. 483–488.
Buu-Hoi et al., "Chemical Abstracts", vol. 69, 1968, col. 106408d.
Abramochkin et al., "Khim. Farm. Zh.", vol. 4(7), 1970, pp. 10–13.
Konshin et al., "Khim. Farm. Zh.", vol. 5(11), 1971, pp. 10–12.
Konshin et al., "Khim. Kihm. Tekhnol", vol. 15(2), 1972, pp. 243–244.
Konshin et al., "Khim. Kihm. Tekhnol", vol. 15(5), 1972, pp. 726–727.
Konshin et al., "Khim. Geterotsikl. Soedin", No. 4, 1973, pp. 531–534.
Konshin et al., "Khim. Farm. Zh.", vol. 8(7), 1989, pp. 17–19.

Primary Examiner—Richard L. Raymond
Assistant Examiner—James H. Turnipseed
Attorney, Agent, or Firm—Tatsuya Ikeda

[57] ABSTRACT

There are described compounds of the formula

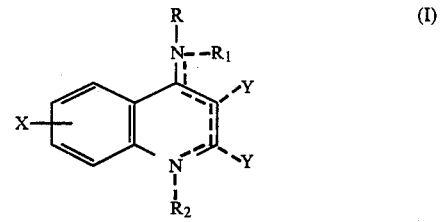

where
—R is

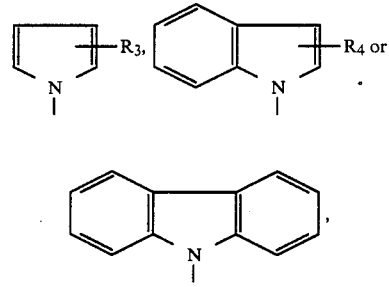

—$R_3$ and $R_3$ being independently —H, loweralkyl, —CHO, —CH=$CH_2$, —CH=CH—loweralkyl, —CH=$CHCO_2C_2H_5$, —$CH_2N(C_2H_5)_2$ or

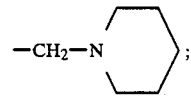

—$R_1$ when existent is —H, loweralkyl, —$CH_2C\equiv CH$,

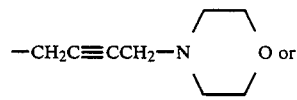

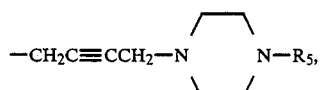

$R_5$ being methyl or phenyl optionally mono-substituted with loweralkyl or loweralkoxy;
—$R_2$ when existent is loweralkyl or —$CH_2C\equiv CH$;
—X is —H, loweralkyl, loweralkoxy, halogen or trifluoromethyl; and the two —Y groups when existent are both —H, or combine to constitute —$(CH_2)_4$—;
which compounds are useful as analgesic agents, and for treating various memory dysfunctions characterized by decreased cholinergic function such as Alzheimer's disease.

56 Claims, No Drawings

N-HETEROARYL-4-QUINOLINAMINES

The present invention relates to compounds of the formula,

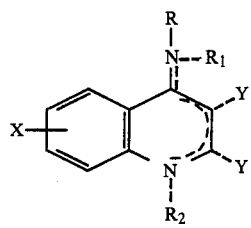

where
—R is

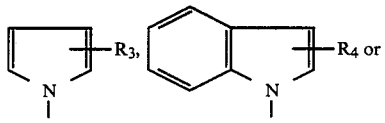

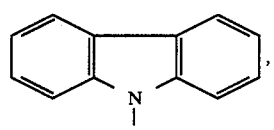

—$R_3$ and $R_4$ being independently —H, loweralkyl, —CHO, —CH=$CH_2$, —CH=CH—loweralkyl, —CH=$CHCO_2C_2H_5$, —$CH_2N(C_2H_5)_2$ or

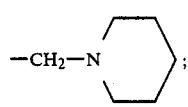

—$R_1$ when existent is —H, loweralkyl, —$CH_2$C≡CH,

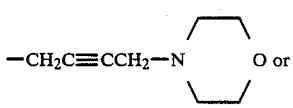

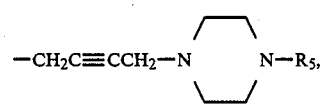

$R_5$ being methyl or phenyl optionally mono-substituted with loweralkyl or loweralkoxy;
—$R_2$ when existent is loweralkyl or —$CH_2$C≡CH;
—X is —H, loweralkyl, loweralkoxy, halogen or trifluoromethyl; and the two —Y groups when existent are both —H, or combine to constitute —$(CH_2)_4$—;

which compounds are useful as analgesic agents and for treating various memory dysfunctions characterized by decreased cholinergic function such as Alzheimer's disease.

Throughout the specification and appended claims, a given chemical formula or name shall encompass all stereo, optical, and geometrical isomers thereof where such isomers exist, as well as pharmaceutically acceptable acid addition salts thereof and solvates thereof such as for instance hydrates.

The dotted lines present in Formula I signify the fact that Formula I encompasses Formula Ia and Formula Ib depicted below. Thus, when the group $R_1$ is present, the group $R_2$ is absent and the two Y groups are present. When the group $R_1$ is absent, the two Y groups are also absent and the group $R_2$ is present.

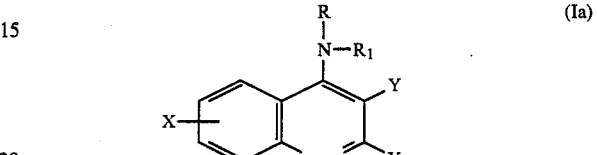

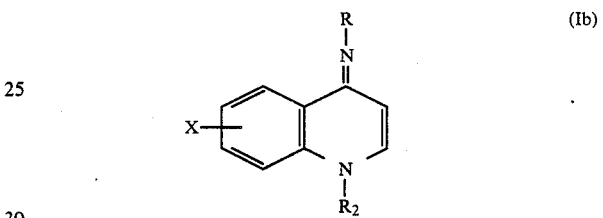

In light of the definition of the group Y, the formula Ia encompasses Formula Ic and Formula Id depicted below.

In light of the definition of the group R, structure Ia also encompasses Formula Ie, Formula If and Formula Ig depicted below.

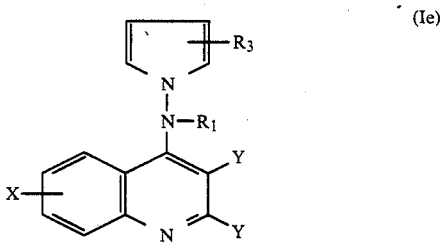

-continued

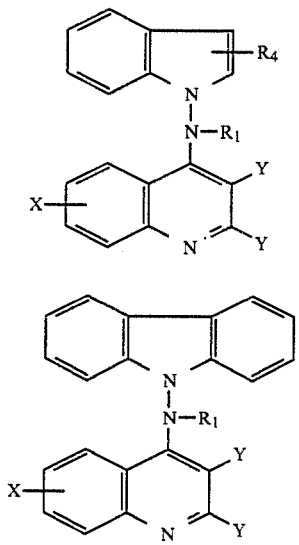

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, sec-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

The compounds of Formula I of this invention can be synthesized by following or combining one or more of the steps described below. Throughout the description of the synthetic steps, the definitions X, Y, R and $R_1$ through $R_5$ are as given above unless otherwise stated or indicated, and other nomenclatures appearing below shall have the same meanings defined in their respective appearances unless otherwise stated or indicated.

STEP A

A compound of Formula II is allowed to react with a compound of Formula III where —$R_6$ is

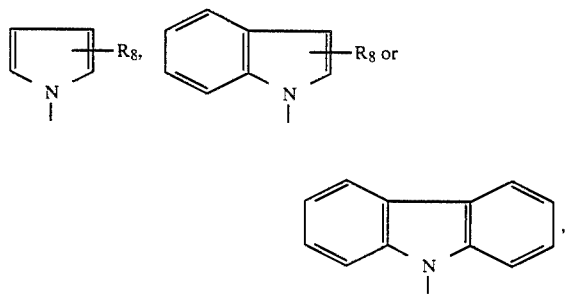

$R_8$ being —H or loweralkyl; and $R_7$ is —H or loweralkyl, to afford a compound of Formula IV.

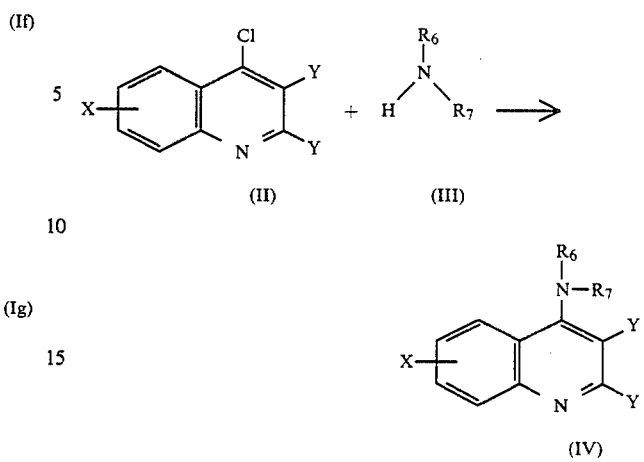

Said reaction is typically conducted in a suitable solvent such as isopropanol at a temperature of between about 20° C. and 150° C. It is convenient to add a small amount of ethereal HCl to the reaction system.

STEP B

As an alternative to STEP A, a compound of Formula IVa obtained from STEP A is treated with a strong base such as sodium hydride or potassium hydride in a suitable solvent such as a polar aprotic solvent (dimethylformamide, dimethylsulfoxide, ethers, etc.) or aromatic hydrocarbon at a temperature of between about −10° and 50°, preferably 0°–25° to form the anion of IVa, which is reacted with a chloride or bromide compound of the Formula $R_9$—W, where $R_9$ is loweralkyl or —$CH_2C\equiv CH$ and W is chlorine or bromine, at a temperature of between −10° and 80°, preferably between 0° and 25° to obtain a compound of Formula V.

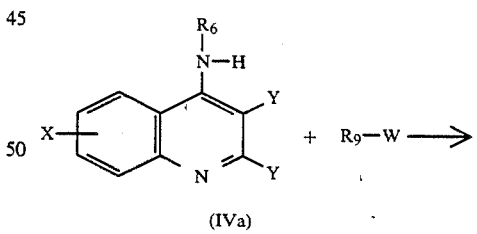

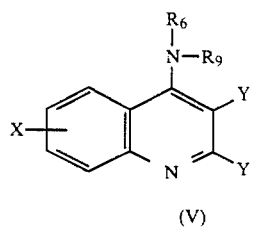

During the reaction described above, another product having Formula VI is also obtained along with compound V. The two products can be separated from each other in a suitable manner known to the art.

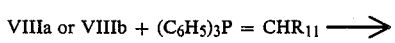

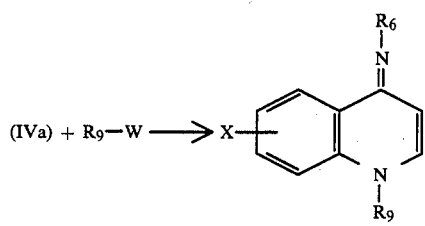

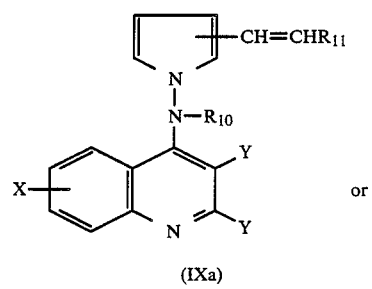

STEP C

A compound of Formula VIIa or VIIb where —$R_{10}$ is —H, loweralkyl or —$CH_2C\equiv CH$ obtained from one of the foregoing steps is allowed to react with phosphorus oxychloride and dimethylformamide to afford a compound of Formula VIIIa or VIIIb, respectively.

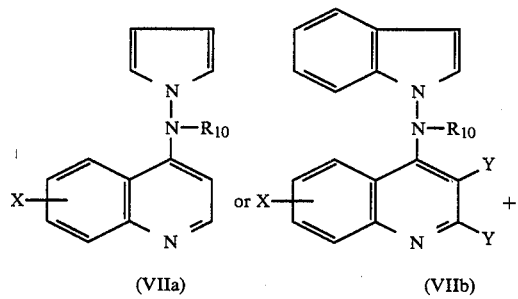

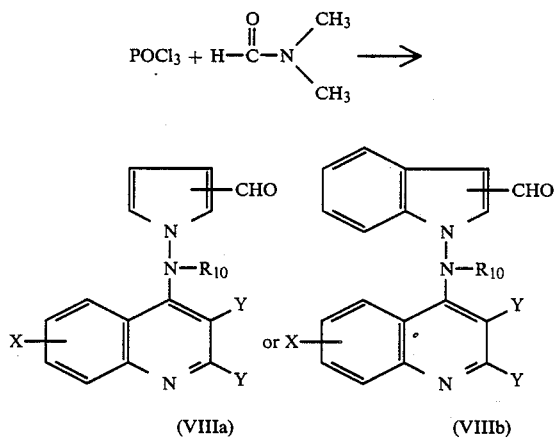

Said reaction can be conducted under conditions usually used for carrying out Vilsmeier reactions. Typically, it is conducted in a suitable solvent such as halogenated hydrocarbon at a temperature of about 20°–100° C.

The two positional isomers obtained above (namely, the product in which the formyl group is at the 2-position of the pyrrole ring and the one in which the formyl group is at the 3-position) can be separated from each other in a suitable manner known to the art.

STEP D

Compound VIIIa or VIIIb is subjected to Wittig reaction with an ylide of the Formula $(C_6H_5)_3P=CHR_{11}$ where $R_{11}$ is hydrogen or loweralkyl to afford a compound of Formula IXa or IXb, respectively.

The above reaction can be conducted under conditions usually used for carrying out Wittig reactions. Thus, the ylide is prepared in a routine manner known to the art from methyl or loweralkyl triphenylphosphonium bromide and a suitable base such as sodium hydride, potassium tert-butoxide or n-butyllithium in a suitable solvent including anhydrous ethereal solvents such as 1,2-dimethoxyethane and diethyl ether. Thereafter a solution of compound VIIIa or VIIIb in a suitable solvent such as anhydrous ether is added to the freshly prepared ylide solution and the mixture is stirred at a temperature of between about −10° C. and 80° C.

STEP E

Compound VIIIa or VIIIb is allowed to react with triethyl phosphonoacetate and a strong base such as sodium hydride in substantially the same manner as in STEP D to afford a compound of Formula Xa or Xb, respectively (Horner-Emmons reaction).

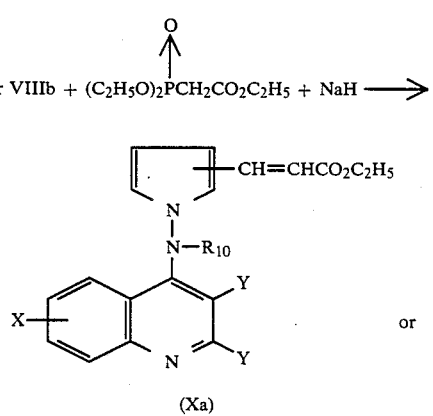

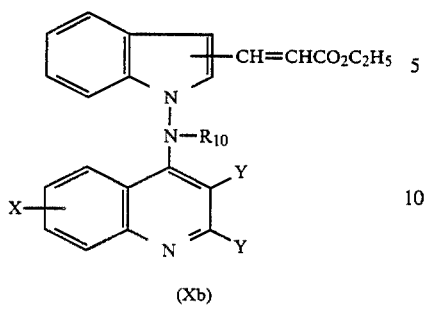

(Xb)

STEP F

Compound IXa or IXb is hydrogenated in the presence of a suitable catalyst such as Pd/C or Pt/C and a suitable medium such as ethanol at a temperature of 25° to 80° C. to afford a compound of Formula XIa or XIb, respectively.

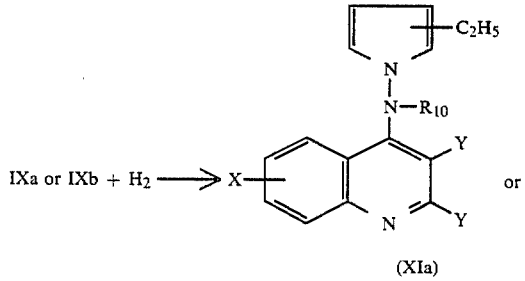

(XIa)

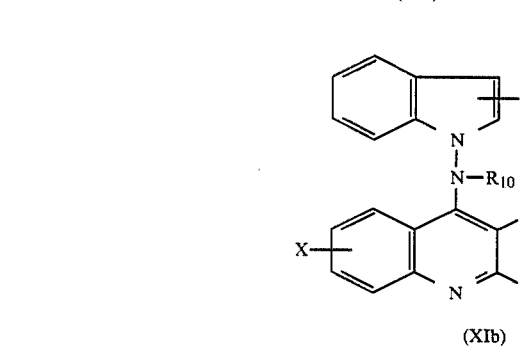

(XIb)

STEP G

Compound VIIIa is allowed to react with formaldehyde and diethylamine or piperidine to afford a compound of Formula XII or XIII, respectively (Mannich reaction). This reaction is typically conducted in a suitable solvent such as 1,4-dioxane or ethanol at a temperature of 25° to 100° C.

VIIIa + (CH$_2$O)$_n$ + HN(C$_2$H$_5$)$_2$ or H—N⟨ ⟩ →

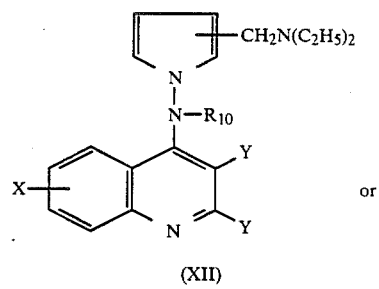

(XII)

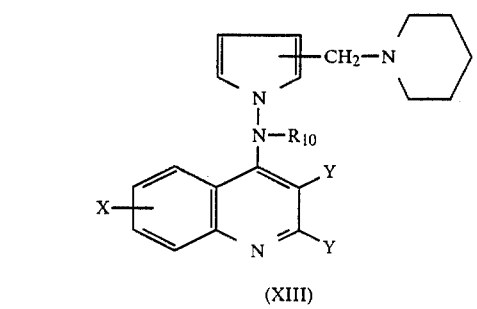

(XIII)

Similarly, Compound VIIIb is allowed to react with formaldehyde and diethylamine or piperidine to afford a compound of Formula XIV or XV, respectively. This reaction is conducted in substantially the same manner as above.

VIIIb + (CH$_2$O)$_n$ + HN(C$_2$H$_5$)$_2$ or H—N⟨ ⟩ →

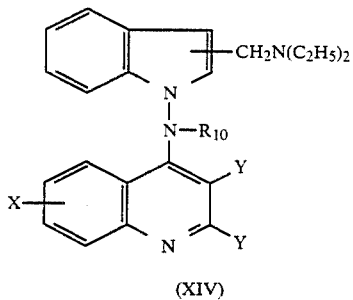

(XIV)

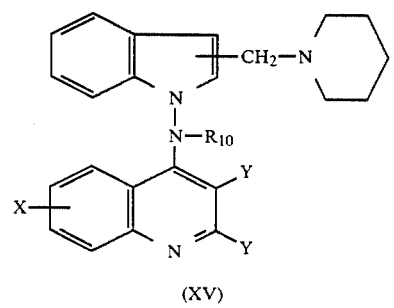

(XV)

STEP H

Compound Va obtained from STEP B is allowed to react with formaldehyde and morpholine or a secondary amine of Formula XVI to afford a compound of Formula XVII or XVIII, respectively (Mannich reaction). This reaction is conducted in substantially the same manner as in STEP G.

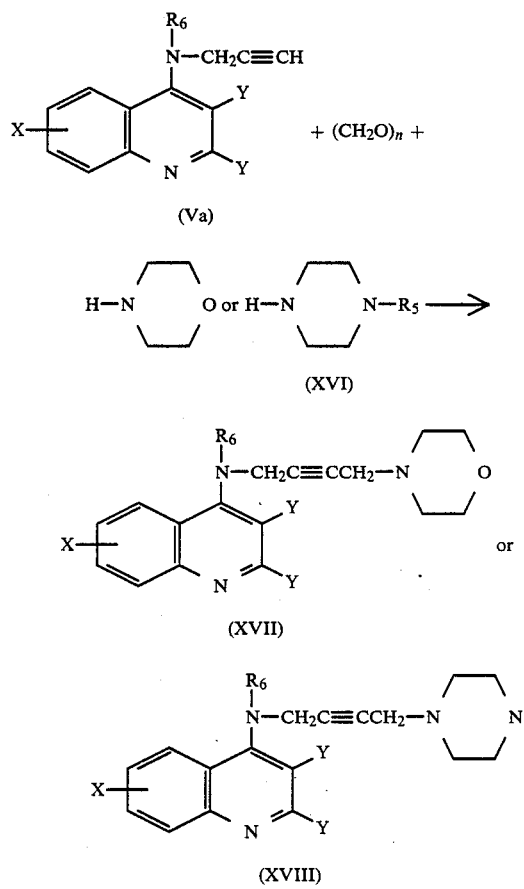

Compounds I of the present invention are useful as analgesic agents due to their ability to alleviate pain in mammals. The activity of the compounds is demonstrated in the 2-phenyl-1,4-benzoquinone-induced writhing (PQW) test in mice, a standard assay for analgesia [Proc. Soc. Exptl. Biol. Med., 95, 729 (1957)].

The results of some of the compounds of this invention (expressed in terms of percent inhibition at 20 mg/kg, s.c.) are shown in Table 1 along with that of a prior art compound.

TABLE 1

| ANALGESIC ACTIVITY | |
|---|---|
| Compound | PQW Percent inhibition at 20 mg/kg,s.c. |
| N-(1H-pyrrol-1-yl)-7-trifluoromethyl-4-quinolinamine hydrochloride | 48% |
| N-(1H-indol-1-yl)-4-quinolinamine maleate | 32% |
| N-(1H-pyrrol-1-yl)-4-quinolinamine hydrochloride | 26% |
| N-propyl-N-(1H-pyrrol-1-yl)-4-quinolinamine maleate | 33% |
| N-(1H-pyrrol-1-yl)-1,2,3,4-tetrahydro-9-acridinamine hydrochloride | 43% |
| N-(4-quinolinyl)-9H-carbazol-9-amine hydrochloride | 30% |
| 1-[7-chloro-4-quinolinyl)-propylamino]-1H-pyrrole-2-carboxaldehyde | 31% |
| 7-chloro-N-propyl-N- | 42% |

TABLE 1-continued

| ANALGESIC ACTIVITY | |
|---|---|
| Compound | PQW Percent inhibition at 20 mg/kg,s.c. |
| (1H-pyrrol-1-yl)-4-quinolinamine maleate | |
| 1-[(7-chloro-4-quinolinyl)-propylamino]-1H-pyrrole-3-carboxaldehyde | 42% |
| 7-chloro-1-(2-propynyl)-N-(1H-pyrrol-1-yl)-4(1H)-quinolinamine | 48% |
| 7-chloro-N-(2-diethylaminomethyl-1H-pyrrol-1-yl)-4-quinolinamine | 55% |
| N-(3-methyl-1H-indol-1-yl)-4-quinolinamine hydrochloride | 44% |
| N-propyl-N-(4-quinolinyl)-9H-carbazol-9-amine | 55% |
| N-(3-Methyl-1H-indol-1-yl)-N-propyl-1,2,3,4-tetrahydro-9-acridinamine | 42% |
| 7-chloro-N-[2-(1-piperidinyl)-methyl-1H-pyrrol-1-yl]-4-quinolinamine (Reference Compound) | 35% |
| Propoxyphene | 50% at 3.9 mg/kg,s.c. |

Compounds I of the present invention are also useful for the treatment of various memory dysfunctions characterized by decreased cholinergic function such as Alzheimer's disease.

This utility is demonstrated by the ability of these compounds to restore cholinergically deficient memory in the Dark Avoidance Assay, where they are in general active over a broader dose range than heretofore known compounds, a distinct therapeutic advantage. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Test results of scopolamine-induced Dark Avoidance Assay for representative compounds of this invention are presented in Table 2 along with that of a reference compound.

TABLE 2

| DARK AVOIDANCE ASSAY | | |
|---|---|---|
| Compound | Dose (mg/ kg of body weight,s.c.) | % of Animals with Scopolamine Induced Memory Deficit Reversal |
| N-(1H-pyrrol-1-yl)-7-trifluoromethyl-4- | 1.25 | 40% |

TABLE 2-continued

DARK AVOIDANCE ASSAY

| Compound | Dose (mg/kg of body weight,s.c.) | % of Animals with Scopolamine Induced Memory Deficit Reversal |
|---|---|---|
| quinolinamine hydrochloride N-(1H-pyrrol-1-yl)-4-quinolinamine hydrochloride | 0.16 | 47% |
| N-propyl-N-(1H-pyrrol-1-yl)-4-quinolinamine maleate | 0.16 | 33% |
| N-(1H-pyrrol-1-yl)-1,2,3,4-tetrahydro-9-acridinamine hydrochloride | 0.63 | 20% |
| 7-chloro-N-propyl-N-(1H-pyrrol-1-yl)-4-quinolinamine maleate (Reference Compound) | 0.31 | 20% |
| Physostigmine | 0.31 | 20% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tables. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the compounds of this invention include:
N-(1H-Pyrrol-1-yl)-4-quinolinamine;
7-Chloro-N-(1H-pyrrol-1-yl)-4-quinolinamine;
N-(1H-Pyrrol-1-yl)-7-trifluoromethyl-4-quinolinamine;
N-Methyl-N-(1H-pyrrol-1-yl)-4-quinolinamine;
7-Chloro-N-methyl-N-(1H-pyrrol-1-yl)-4-quinolinamine;
N-(1H-Pyrrol-1-yl)-7-trifluoromethyl-4-quinolinamine;
7-Chloro-N-propyl-N-(1H-pyrrol-1-yl)-4-quinolinamine;
N-(1H-Indol-1-yl)-4-quinolinamine;
N-(3-Methyl-1H-indol-1-yl)-4-quinolinamine;
7-Chloro-N-(1H-indol-1-yl)-N-propyl-4-quinolinamine;
N-(1H-Pyrrol-1-yl)-1,2,3,4-tetrahydro-9-acridinamine;
N-(1H-Indol-1-yl)-1,2,3,4-tetrahydro-9-acridinamine;
N-(3-Methyl-1H-indol-1-yl)-1,2,3,4-tetrahydro-9-acridinamine;
N-(4-Quinolinyl)-9H-carbazol-9-amine;
N-(2-Methyl-1H-indol-1-yl)-1,2,3,4-tetrahydro-9-acridinamine;
N-Propyl-N-(1H-pyrrol-1-yl)-4-quinolinamine;
1-Propyl-N-(1H-pyrrol-1-yl)-4(1H)-quinolinimine;
7-Chloro-N-(2-propynyl)-N-(1H-pyrrol-1-yl)-4-quinolinamine;
7-Chloro-1-(2-propynyl)-N-(1H-pyrrol-1-yl)-4(1H)-quinolinimine;
N-(3-Methyl-1H-indol-1-yl)-N-propyl-1,2,3,4-tetrahydro-9-acridinamine;
N-Propyl-N-(4-quinolinyl)-9H-carbazol-9-amine;
N-(9H-Carbazol-9-yl)-1-propyl-4(1H)-quinolinimine;
1-(Methyl-4-quinolinamino)-1H-pyrrole-2-carboxaldehyde;
1-(Methyl-4-quinolinamino)-1H-pyrrole-3-carboxaldehyde;
1-[(7-Chloro-4-quinolinyl)methylamino]-1H-pyrrole-2-carboxaldehyde;
1-[(7-Chloro-4-quinolinyl)methylamino]-1H-pyrrole-3-carboxaldehyde;
1-[(7-Chloro-4-quinolinyl)propylamino]-1H-pyrrole-2-carboxaldehyde;
1-[(7-Chloro-4-quinolinyl)propylamino]-1H-pyrrole-3-carboxaldehyde;
N-Methyl-N-(2-ethenyl-1H-pyrrol-1-yl)-4-quinolinamine;
7-Chloro-N-(2-ethenyl-1H-pyrrol-1-yl)-N-methyl-4-quinolinamine;
7-Chloro-N-propyl-N-(2-ethenyl-1H-pyrrol-1-yl)-4-quinolinamine;
3-[1-(Methyl-4-quinolinylamino)-1H-pyrrol-2-yl]-2-propenoic acid, ethyl ester;

3-[1-[(7-Chloro-4-quinolinyl)methylamino]-1H-pyrrol-2-yl]-2-propenoic acid, ethyl ester;
N-Methyl-N-(2-ethyl-1H-pyrrol-1-yl)-4-quinolinamine;
7-Chloro-N-(2-ethyl-1H-pyrrol-1-yl)-N-methyl-4-quinolinamine;
7-Chloro-N-(2-diethylaminomethyl-1H-pyrrol-1-yl)-4-quinolinamine;
N-(2-diethylaminomethyl-1H-pyrrol-1-yl)-N-methyl-7-trifluoromethyl-4quinolinamine;
7-Chloro-N-[2-(1-piperidinyl)methyl-1H-pyrrol-1-yl]-4-quinolinamine;
7-Chloro-N-[4-(4-methylpiperazin-1-yl)-2-butynyl]-N-(1H-pyrrol-1-yl)-4-quinolinamine; and
7-Chloro-N-[4-[4-(2-methoxyphenylpiperazin-1-yl]-2-butynyl-N-(1H-pyrrol-1-yl)-4-quinolinamine;

The following examples are presented in order to illustrate this invention.

EXAMPLE 1

N-(1H-Pyrrol-1-yl)-4-quinolinamine hydrochloride

A solution of 4-chloroquinoline (10 g) and 1-aminopyrrole (6 g) in 100 ml isopropanol containing 1 ml saturated ether/HCl was stirred at 80° for thirty minutes, and thereafter cooled, stirred with water, basified with sodium carbonate and extracted with dichloromethane. The organic extract was washed successively with water and saturated sodium chloride solution, dried (anhy. $MgSO_4$), filtered and concentrated to 12 g of solid, m.p. 165°–168°. Four grams were converted to the hydrochloride salt and recrystallized twice from methanol/ether to give 2.9 g crystals, m.p. 233°–234°.

ANALYSIS:

| | | |
|---|---|---|
| Calculated for $C_{13}H_{11}N_3.HCl$: | 63.54% C 4.92% H 17.11% N | |
| Found: | 63.10% C 5.01% H 16.99% N | |

EXAMPLE 2

7-Chloro-N-(1H-pyrrol-1-yl)-4-quinolinamine hydrochloride

To a solution of 4,7-dichloroquinoline (5.0 g) in 100 ml of isopropanol were added 1-aminopyrrole (2.46 g) and 1 ml of ether/HCl. The mixture was heated to 80° C. and stirred for one hour. The mixture was then poured into water and extracted with DCM (3×). The combined extracts were washed with water and dried (sat. NaCl, anhy. $MgSO_4$).

After filtration, the solvent was evaporated to yield a solid (5.54 g), which was recrystallized from 10% ethyl acetate/DCM to give a solid (3.3 g). This material was dissolved in methanol and the solution was acidified to pH 1 with ether/HCl. The resulting precipitate was collected to yield 2.7 g solid, m.p. 250°–251° C. (decomp.).

ANALYSIS:

| | |
|---|---|
| Calculated for $C_{13}H_{10}ClN_3.HCl$: | 55.71% C 3.93% H 15.00% N |
| Found: | 55.56% C 3.98% H 14.95% N |

EXAMPLE 3

N-(1H-Pyrrol-1-yl)-7-trifluoromethyl-4-quinolinamine hydrochloride

A solution of 4-chloro-7-(trifluoromethyl)quinoline (5 g) and 1H-pyrrol-1-amine (2.1 g) in 100 ml of isopropanol containing 1 ml saturated ether/HCl was stirred for thirty minutes at reflux, and thereafter was cooled, stirred with water, basified with sodium carbonate and extracted with ether. The organic extract was washed successively with water and saturated sodium chloride solution, dried (anhy. $MgSO_4$), filtered and concentrated to 6.5 g solid. This was converted to the hydrochloride salt and recrystallized twice from methanol/ether to give 2.4 g white crystals, 260° dec.

ANALYSIS:

| | |
|---|---|
| Calculated for $C_{14}H_{10}F_3N_3.HCl$: | 53.60% C 3.53% H 13.40% N |
| Found: | 53.68% C 3.39% H 13.64% N |

EXAMPLE 4

N-Methyl-N-(1H-pyrrol-1-yl)-4-quinolinamine maleate

To a stirred solution prepared from 4-chloroquinoline (25 g), ether/HCl (1 ml) and 150 ml of isopropanol was added dropwise 1-methylaminopyrrole (15.86 g) in 20 ml of isopropanol. This mixture was then heated to 70° C. and stirred for three hours.

The mixture was then cooled, poured into water, and basified with $Na_2CO_3$ (aq). The aqueous mixture was then extracted with ethyl acetate and the organic layer was washed with water and dried (sat. NaCl, anhy. $MgSO_4$).

After filtration, the solvent was evaporated to yield an oil (37.83 g), which was eluted with 50% ethyl acetate/DCM on silica gel columns via HPLC (High Pressure Liquid Chromatography). The desired functions were concentrated to yield an oil which solidified on standing (30.7 g), m.p. 101°–104° C. A 3 g sample of this material was dissolved in methanol and acidified with maleic acid. The resulting precipitate was collected to yield a solid (4.02 g) which was recrystallized from ethanol (100%). The resulting crystals were collected to yield 3.3 g solid, m.p. 190°–192° C.

ANALYSIS:

| | |
|---|---|
| Calculated for $C_{14}H_{13}N_3.C_4H_4O_4$: | 63.72% C 5.01% H 12.39% N |
| Found: | 63.57% C 5.09% H 12.32% N |

EXAMPLE 5

7-Chloro-N-methyl-N-(1H-pyrrol-1-yl)-4-quinolinamine hydrochloride

To 275 ml isopropanol was added 4,7-dichloroquinoline (25 g), followed by 2 ml ethereal HCl. Then to the resultant solution was added a solution of N-methylaminopyrrole (15 g) in 25 ml isopropanol.

The mixture was stirred at reflux (95° C.) for five hours, and thereafter was poured into one liter of ice-water and stirred for five minutes. The pH was adjusted to 10 with $Na_2CO_3$ and the mixture was extracted with ethyl acetate (2×). The organic layer was washed with water and dried (saturated NaCl, anhydrous $MgSO_4$).

After filtration, the solvents were evaporated to yield an oil (32 g) which was eluted on a silica gel column with ethyl acetate/DCM (1:1) via HPLC. The desired fractions were combined and concentrated to an oil, which solidified on standing to give 29.6 g, m.p. 82°–83° C.

A sample of this material (3.5 g) was dissolved in 100 ml ethanol, and the solution was acidified to pH 1 with ethereal HCl. After dilution with 30 ml ether, the resultant precipitate was collected and dried to give 3.4 g, dec. at 225° C. This material was recrystallized from ethanol/ether (1:1) to give 2.5 g of solid, dec. at 230° C.

| ANALYSIS: | |
|---|---|
| Calculated for $C_{14}H_{12}ClN_3 \cdot HCl$: | 57.16% C 4.45% H 14.28% N |
| Found: | 56.72% C 4.47% H 14.14% N |

EXAMPLE 6

N-(1H-Pyrrol-1-yl)-7-trifluoromethyl-4-quinolinamine maleate

To a solution prepared from 4-chloro-7-trifluoromethyl quinoline (25 g), 1 ml of ethereal HCl and 150 ml of isopropanol was added dropwise 1-methylaminopyrrole (11.63) in 40 ml of isopropanol. The mixture was heated to 90° C. and stirred for four hours, and thereafter cooled, poured into water and basified with $Na_2CO_3$ (aq). The aqueous mixture was then extracted with ethyl acetate and the organic layer was washed with water and dried (sat. NaCl, anhy. $MgSO_4$).

After filtration, the solvent was evaporated to yield a solid (33 g) which was eluted with 10% ethyl acetate/DCM on silica gel columns via HPLC. The desired fractions were concentrated to yield an oil (33 g). A 5.5 g sample of this material was dissolved in ethanol and acidified with maleic acid. The resulting precipitate was collected to yield 3.3 g of solid, m.p. 165°–167° C.

| ANALYSIS: | |
|---|---|
| Calculated for $C_{15}H_{12}F_3N_3 \cdot C_4H_4O_4$: | 56.02% C 3.93% H 10.32% N |
| Found: | 56.02% C 3.94% H 10.30% N |

EXAMPLE 7

7-Chloro-N-propyl-N-(1H-pyrrol-1-yl)-4-quinolinamine maleate

To a mixture of 4,7-dichloroquinoline (5.0 g) and ether/HCl (1 ml) in 100 ml of isopropanol was added dropwise N-propylaminopyrrole (3.47 g) in 20 ml of isopropanol. This mixture was heated to 70° C. and stirred for six hours.

The mixture was poured into water, basified with $Na_2CO_3$ (aq) and stirred for five minutes. The aqueous layer was extracted with ethyl acetate and the organic layer was washed with water and dried (sat. NaCl, anhy. $MgSO_4$).

After filtration, the solvent was evaporated to yield an oil (8.83 g) which was eluted with 10% ethyl acetate/DCM on a silica gel column via HPLC. The desired fractions were concentrated to yield an oil which solidified on standing (3.5 g). This material was dissolved in ethyl acetate/methanol (10:1) and acidified with maleic acid. The resulting precipitate was collected to yield 3.18 g solid, m.p. 156°–159° C.

| ANALYSIS: | |
|---|---|
| Calculated for $C_{16}H_{16}ClN_3 \cdot C_4H_4O_4$: | 59.78% C 4.98% H 10.46% N |
| Found: | 59.74% C 5.12% H 10.43% N |

EXAMPLE 8

N-(1H-Indol-1-yl)-4-quinolinamine maleate

A solution prepared from 4-chloro-quinoline (5 g), 1H-indol-1-amine (5 g), 100 ml isopropanol and 1 ml saturated ether/HCl was stirred for three hours at reflux, and thereafter cooled, stirred with water, basified with sodium carbonate and extracted with dichloromethane. The organic extract was washed successively with water and saturated sodium chloride solution, dried (anhy. $MgSO_4$), filtered and concentrated to a solid. This was purified by flash chromatography (silica, 10% ethyl acetate in dichloromethane) to give 6.5 g solid, m.p. 128° C. This was converted to the maleate salt in methanol to give 7.4 g of crystals, m.p. 207°–208° C. dec. Three grams were recrystallized from methanol/ether to give 2.6 g crystals, m.p. 209°–210° dec.

| ANALYSIS: | |
|---|---|
| Calculated for $C_{17}H_{13}N_3 \cdot C_4H_4O_4$: | 67.19% C 4.57% H 11.20% N |
| Found: | 67.17% C 4.80% H 11.43% N |

EXAMPLE 9

N-(3-Methyl-1H-indol-1-yl)-4-quinolinamine hydrochloride

To a solution prepared from 4-chloroquinoline (9.81 g), 200 ml of isopropanol and 1 ml of ether/HCl was added 3-methyl-1H-indolamine (19 g, 45% pure) and this mixture was heated to 80° C. and stirred for six hours. The mixture was cooled, poured into water and basified with $Na_2CO_3$ (aq). The basic aqueous mixture was then extracted with ethyl acetate (3×), and the organics were combined, washed with water and dried (sat. NaCl, anhy. $MgSO_4$).

After filtration, the solvent was evaporated to a solid (26 g), which was eluted with 20% ethyl acetate/DCM on two silica gel columns via HPLC. The desired fractions were concentrated to yield a solid (3.5 g), which was dissolved in ethanol and acidified with ether/HCl. The resulting precipitate was collected to yield a solid (2.8 g), which was recrystallized from methanol/ether (1:5) to yield 2.2 g of solid, m.p. 196°–200° C.

| ANALYSIS: | |
|---|---|
| Calculated for $C_{18}H_{15}N_3 \cdot HCl$: | 69.79% C 5.17% H 13.57% N |
| Found: | 69.32% C 5.13% H 13.34% N |

EXAMPLE 10

7-Chloro-N-(1H-indol-1-yl)-N-propyl-4-quinolinamine maleate

To 50 ml 1-methyl-2-pyrrolidinone, were added successively 4,7-dichloroquinoline (4.5 g), 1 ml ethereal HCl and a solution of N-(1H-indol-1-yl)-N-propylamine (4.0 g) in 30 ml 1-methyl-2-pyrrolidinone.

The mixture was stirred at 130° C. for seven hours, and thereafter poured into 500 ml iced water. The pH was adjusted to 10 with a $Na_2CO_3$ solution and the mixture was extracted with ether (3×). The ether solution was washed with water and dried (saturated NaCl, anhydrous $MgSO_4$).

After filtration, the solvent was evaporated to yield 2.3 g of thick oil, which was eluted on a silica gel column with 1% methanol/DCM via HPLC. The desired fractions were combined and concentrated to yield 2.0 g of oil, which was dissolved in ethanol and acidified to pH 1 with ethereal maleic acid. The resultant precipitate was collected and dried to give 2.1 g, m.p. 137°–138° C.

ANALYSIS:

| | |
|---|---|
| Calculated for $C_{20}H_{18}ClN_3 \cdot C_4H_4O_4$: | 63.79% C 4.91% H 9.30% N |
| Found: | 63.68% C 4.76% H 9.18% N |

EXAMPLE 11

N-(1H-Pyrrol-1-yl)-1,2,3,4-tetrahydro-9-acridinamine hydrochloride

A solution prepared from 9-chloro-1,2,3,4-tetrahydroacridine[1] (5.5 g), 1H-pyrrol-1-amine (2.5 g), 100 ml isopropanol and 1 ml saturated ether/HCl was stirred at reflux for one hour, and thereafter cooled, diluted with ether and filtered to give 5.7 g of solid. This was recrystallized from methanol/ether to give 4 g white solid, m.p. 305° dec.

[1] J. Org. Chem. 11, 359 (1946)

ANALYSIS:

| | |
|---|---|
| Calculated for $C_{17}H_{17}N_3 \cdot HCl$: | 68.10% C 6.05% H 14.02% N |
| Found: | 68.17% C 6.07% H 14.09% N |

EXAMPLE 12

N-(1H-Indol-1-yl)-1,2,3,4-tetrahydro-9-acridinamine hydrochloride

A solution prepared from 9-chloro-1,2,3,4-tetrahydroacridine[1] (16 g), 1H-indol-1-amine[2] (12 g), 125 ml of isopropanol and 5 ml saturated ether/HCl was stirred at reflux for six hours, and thereafter cooled, stirred with water, basified with sodium carbonate and extracted with dichloromethane. The organic extract was washed successively with water and saturated sodium chloride solution, dried (anhy. $MgSO_4$), filtered and concentrated to 30 g of oil. This oil was purified twice by flash chromatography to give 16 g solid, m.p. 190°–194° C. Four grams were converted to the hydrochloride salt and recrystallized twice from methanol/ether to give 3 g solid, dec. 270°–272° C.

[1] J. Org. Chem. 11, 359 (1946).
[2] Tet. Lett. No. 5, 461 (1974).

ANALYSIS

| | | | |
|---|---|---|---|
| Calculated for $C_{21}H_{19}N_3 \cdot HCl$ | 72.09% C | 5.76% H | 12.01% N |
| Found | 71.89% C | 5.92% H | 12.05% N |

EXAMPLE 13

N-(3-Methyl-1H-indol-1-yl)-1,2,3,4-tetrahydro-9-acridinamine hydrochloride

To a mixture of 3-methyl-1H-indol-1-amine (11.03 g, 45% pure) and 100 ml of isopropanol was added a solution of 9-chloro-1,2,3,4-tetrahydroacridine hydrochloride (9.4 g) and this mixture was heated to 80° C. and stirred for six hours. The mixture was cooled, poured into water, basified with $Na_2CO_3$ (aq), and then extracted with ethyl acetate. The organic layer was washed with water and dried (sat. NaCl, anhy. $MgSO_4$).

After filtration, the solvent was evaporated to yield an oil (16.79 g), which was eluted first with DCM and then with ether/petroleum ether (1:1) on a silica gel column via HPLC. The desired fractions were concentrated to yield 4.08 g solid. Of this material, 3.0 g was dissolved in ethanol and acidified with ethereal HCl. The resulting precipitate was collected to yield a solid (3.3 g) which was recrystallized from methanol/ether (1:10) to yield 2.2 g of solid, m.p. >250° C.

ANALYSIS

| | | | |
|---|---|---|---|
| Calculated for $C_{22}H_{21}N_3 \cdot HCl$ | 72.62% C | 6.05% H | 11.55% N |
| Found | 72.19% C | 6.17% H | 11.43% N |

EXAMPLE 14

N-(4-Quinolinyl)-9H-carbazol-9-amine hydrochloride

A solution of 9H-carbazol-9-amine (11 g, as an unquantified mixture with carbazole) and 4-chloroquinoline (10 g) in 100 ml isopropanol acidified with ether/HCl was refluxed for seven hours, and thereafter cooled, stirred with water, basified with sodium carbonate and extracted with ethyl acetate. The organic extract was washed successively with water and saturated sodium chloride solution, dried (anhy. $MgSO_4$), filtered and concentrated to 20 g solid. This material was converted to the hydrochloride salt in methanol/ether to give 6 g solid, m.p. >260°. Three grams were recrystallized from methanol/ether to give 2.6 g white needles, dec. 300°–302°.

ANALYSIS

| | | | |
|---|---|---|---|
| Calculated for $C_{21}H_{15}N_3 \cdot HCl$ | 72.93% C | 4.66% H | 12.15% N |
| Found | 72.64% C | 4.76% H | 12.05% N |

EXAMPLE 15

N-(2-Methyl-1H-indol-1-yl)-1,2,3,4-tetrahydro-9-acridinamine

To 100 ml N-methyl-2-pyrrolidone were added 2-methyl-1H-indol-1-amine (3.5 g), 9-chloro-1,2,3,4-tetrahydroacridine (5.5 g) and a few drops of ethereal HCl.

The mixture was stirred at 160° C. for five hours and poured into 500 ml iced water. The pH was adjusted to 10 with a $Na_2CO_3$ solution and the mixture extracted with ethyl acetate. The organic layer was washed with water and dried (saturated NaCl, anhydrous $MgSO_4$).

After filtration, the solvent was evaporated to yield about 10 g of dark oil which was eluted on a silica gel column with 20% ethyl acetate/DCM via HPLC. The desired fractions were combined and concentrated to an oil, which solidified on cooling to 2.4 g solid, m.p.

134°-137° C. This material was recrystallized from isopropyl ether/hexanes (1:3) to give 2.1 g of crystals, dec. 156°-158° C.

| ANALYSIS | | | |
|---|---|---|---|
| Calculated for $C_{22}H_{21}N_3$ | 80.70% C | 6.47% H | 12.83% N |
| Found | 80.11% C | 6.48% H | 12.40% N |

EXAMPLE 16

N-Propyl-N-(1H-pyrrol-1-yl)-4-quinolinamine

A solution of N-(1H-pyrrol-1-yl)-4-quinolinamine (8.2 g) in 60 ml dimethylformamide was slowly added to an ice cooled suspension of sodium hydride prepared by washing 1.9 g of 60% NaH dispersion in oil with hexanes and suspending the residue in 10 ml of dimethylformamide. After the anion formation, a solution of 1-bromopropane (5.8 g) in 10 ml of dimethylformamide was added. The reaction mixture was stirred two hours and thereafter stirred with ice water and extracted with dichloromethane. The organic extract was washed with water and saturated sodium chloride solution, dried (anhydrous $MgSO_4$), filtered and concentrated to 12 g oil. This oil was purified by flash chromatography to give 4 g oil and 4.4 g of 1-propyl-N-(1H-pyrrol-1-yl)-4(1H)-quinolinimine as a solid. The oil product was converted to the maleate salt and recrystallized twice from methanol/ether to give 3.7 g of needles, 169°-170° d.

| ANALYSIS | | | |
|---|---|---|---|
| Calculated for $C_{16}H_{17}N_3.C_4H_4O_4$ | 65.38% C | 5.76% H | 11.44% N |
| Found | 65.43% C | 5.79% H | 11.51% N |

EXAMPLE 17

1-Propyl-N-(1H-pyrrol-1-yl)-4(1H)-quinolinimine

A solution of N-(1H-pyrrol-1-yl)-4-quinoline (8.2 g) in 60 ml dimethylformamide was slowly added to an ice cooled suspension of sodium hydride prepared by washing 1.9 g of 60% NaH dispersion in oil with hexanes and suspending the residue in 10 ml of dimethylformamide. After the anion formation, a solution of 1-bromopropane (5.8 g) in 10 ml dimethylformamide was added. The reaction mixture was stirred for two hours and thereafter stirred with ice-water and extracted with dichloromethane. The organic extract was washed with water and saturated sodium chloride sodium, dried (anhydrous $MgSO_4$), filtered and concentrated to 12 g oil. This oil was purified by flash chromatography to give 4.4 of 1-propyl-N-(1H-pyrrol-1-yl)-4-(1H)-quinolinimine as a solid, m.p. 115° C. and 4 g of N-propyl-N-(1H-pyrrol-1-yl)-4-quinolinamine as an oil. This solid was again purified by flash chromatography to give 3.2 g of pure product as a solid, m.p. 115°-117° C.

| ANALYSIS | | | |
|---|---|---|---|
| Calculated for $C_{16}H_{17}N_3$ | 76.46% C | 6.82% H | 16.72% N |
| Found | 76.11% C | 6.83% H | 16.73% N |

EXAMPLE 18

7-Chloro-N-(2-propynyl)-N-(1H-pyrrol-1-yl)-4-quinolinamine maleate

To a suspension of NaH prepared by washing 4.8 g of 60% NaH dispersion in oil with hexanes and suspending the residue in 30 ml of DMF and maintained at ice bath temperature was added dropwise 7-chloro-N-(1H-pyrrol-1-yl)-4-quinilinamine (25 g) in 200 ml DMF. After gas evolution had ceased, a solution of propargyl bromide (80% in toluene, 13.4 ml) in 25 ml DMF was added dropwise to the cool mixture. The reaction mixture was stirred at ice temperature for two hours.

The reaction mixture was then poured into water and extracted with ethyl acetate. The organic layer was washed with water and dried (saturated NaCl, anhydrous $MgSO_4$). After filtration, the solvent was evaporated to yield an oil (42 g), which was eluted with DCM on silica gel columns via HPLC. The desired fractions were concentrated to yield a solid (11.68 g). Of this solid, 3.2 g was dissolved in ethyl acetate and acidified with maleic acid. The resulting precipitate was collected to yield 3.2 g of solid, m.p. 147°-149° C.

| ANALYSIS | | | |
|---|---|---|---|
| Calculated for $C_{16}H_{12}ClN_3.C_4H_4O_4$ | 60.23% C | 4.27% H | 10.54% N |
| Found | 59.83% C | 4.08% H | 10.53% N |

EXAMPLE 19

7-Chloro-1-(2-propynyl)-N-(1H-pyrrol-1-yl)-4(1H)-quinolinimine

To a suspension of NaH prepared by washing 11.2 g of 60% NaH dispersion in oil with hexanes and suspending the residue in 50 ml of DMF and maintained at ice bath temperature was added dropwise a solution of 7-chloro-N-(1H-pyrrol-1-yl)-4-quinolinamine (61.5 g) in 250 ml DMF. When gas evolution had ceased, a solution of propargy bromide (80% in toluene, 31.2 ml) in 50 ml DMF was added dropwise, and the reaction was allowed to proceed for one hour. The mixture was poured into water and extracted with ethyl acetate. The organic layer was washed with water and dried (sat. NaCl, anhy. $MgSO_4$).

After filtration, the solvent was evaporated to yield a solid (112.96 g), which was eluted with DCM on silica columns via HPLC. The desired fractions were concentrated to yield a solid (3.0 g). This was recrystallized from isopropyl ether/methanol (5:1) and the resulting crystals were collected to yield 2.15 g of solid, m.p. 181°-183° C.

| ANALYSIS | | | |
|---|---|---|---|
| Calculated for $C_{16}H_{12}ClN_3$ | 68.21% C | 4.26% H | 14.92% N |
| Found | 68.18% C | 4.03% H | 14.83% N |

EXAMPLE 20

N-(3-Methyl-1H-indol-1-yl)-N-propyl-1,2,3,4-tetrahydro-9-acridinamine

To a suspension of NaH prepared by washing 0.64 g of 60% NaH dispersion in oil with hexanes and suspending the residue in 5 ml of DMF and maintained at ice bath temperature was added dropwise N-(3-methyl-1H- indol-1-yl)-1,2,3,4-tetrahydro-9-acridinamine (4.2 g) in 30 ml DMF, dropwise. The reaction mixture was stirred for 15 minutes at ice bath temperature, and thereafter, a solution of 1-bromopropane (1.45 ml) in 20 ml DMF was added dropwise. The reaction was allowed to proceed for 20 hours at room temperature. The mixture was then poured into water and extracted with ethyl acetate. The organic layer was washed with water and dried (sat NaCl, anhy. MgSO$_4$).

After filtration, the solvent was evaporated to yield an oil (6.36 g) which was eluted with 2.5% ethyl acetate/DCM on a silica gel column via HPLC. The desired fractions were concentrated to yield 2.76 g of solid, m.p. 136°–138° C. This material was dissolved in ethyl acetate and acidified with ethereal HCl. The resulting precipitate was collected to yield 1.9 g which was recrystallized from ethyl acetate/ether (5:1) to yield a solid 1.3 g (m.p. 220°–222° C.). This material was converted back to the free base with Na$_2$CO$_3$ to yield 1.1 g solid, m.p. 142°–144° C.

| ANALYSIS | | | |
| --- | --- | --- | --- |
| Calculated for C$_{25}$H$_{27}$N$_3$ | 81.26% C | 7.37% H | 11.37% N |
| Found | 81.05% C | 7.35% H | 11.30% N |

EXAMPLE 21

N-Propyl-N-(4-quinolinyl)-9H-carbazol-9-amine

To a suspension of NaH prepared by washing 0.5 g of 60% NaH dispersion in oil with hexanes and suspending the residue in 20 ml of DMF and maintained at ice bath temperature was added N-(4-quinolinyl)-9H-carbazol-9-amine (3.2 g) in 30 ml DMF, dropwise. The mixture was stirred at ice bath temperature until gas evolution had ceased. Then a solution of 1-bromopropane (1.09 ml) in 5 ml DMF was added dropwise and the reaction mixture was stirred at room temperature for twenty hours. The reaction mixture was poured into water and extracted with ethyl acetate. The organic layer was washed with water and dried (sat. NaCl, anh. MgSO$_4$).

After filtration, the solvent was evaporated to yield an oil (4.9 g), which was eluted with 10% ethyl acetate/DCM on a silica gel column via HPLC. The desired fractions were concentrated to yield 0.40 g solid, m.p. 137°–139° C.

| ANALYSIS | | | |
| --- | --- | --- | --- |
| Calculated for C$_{24}$H$_{21}$N$_3$ | 82.02% C | 6.02% H | 11.96% N |
| Found | 81.86% C | 6.05% H | 11.94% N |

EXAMPLE 22

N-(9H-Carbazol-9-yl)-1-propyl-4(1H)-quinolinimine

To a suspension of NaH prepared by washing 0.5 g of 60% NaH dispersion in oil with hexanes and suspending the residue in 20 ml of DMF and maintained at ice bath temperature was added dropwise N-(4-quinolinyl)-9H-carbazol-9-amine (3.2 g) in 30 ml DMF. The reaction mixture was stirred at ice bath temperature until gas evolution had ceased. Then a solution of 1-bromopropane (1.09 ml) in 5 ml DMF was added dropwise and the reaction mixture was stirred at room temperature for twenty hours. The reaction mixture was poured into water and extracted with ethyl acetate. The organic layer was washed with water and dried (sat NaCl, anhy. MgSO$_4$).

After filtration, the solvent was evaporated to yield an oil (4.9 g) which was eluted with 10% ethyl acetate/DCM on a silica gel column via HPLC. The desired fractions were concentrated to yield 2.0 g, m.p. 174°–176° C.

| ANALYSIS | | | |
| --- | --- | --- | --- |
| Calculated for C$_{24}$H$_{21}$N$_3$ | 82.02% C | 6.02% H | 11.96% N |
| Found | 81.71% C | 6.01% H | 11.78% N |

EXAMPLE 23

1-(Methyl-4-quinolinylamino)-1H-pyrrole-2-carboxaldehyde maleate

To dry DMF (18.25 ml) at ice bath temperature was added phosphorous oxychloride (24.48 ml), dropwise. This mixture was stirred for five minutes and then a solution of N-methyl-N-(1H-pyrrol-1-yl)-4-quinolinamine (27 g) in 250 ml of DCE was added rapidly to the mixture. The reaction mixture was then stirred at room temperature for one hour and then heated to 80° C. and stirred for three hours.

The mixture was cooled, treated with an aqueous solution of NaC$_2$H$_3$O$_2$.3H$_2$O (45 g) and then stirred for fifteen minutes at 70° C. This mixture was then cooled and poured into iced water, which was treated with 50% NaOH aqueous solution (90 ml) and then extracted with DCM (4×). The organics were combined, washed with water and dried (sat. NaCl, anh. MgSO$_4$).

After filtration, the solvent was evaporated to yield an oil (39.3 g) which was eluted with hexane/THF (1:2) on silica gel columns via HPLC. The desired fractions were concentrated to yield a solid (27.4 g) which was eluted with 20% hexane/ether on a silica gel column via flash chromatography. The desired fractions were concentrated to yield 15 g solid, m.p. 118°–122° C. Of this material, 3.0 g was dissolved in ethanol and acidified with maleic acid. The resulting precipitate was collected to yield a solid (3.7 g) which was recrystallized from ethyl acetate/methanol (5:1) to yield 2.8 g solid, m.p. 158°–160° C.

| ANALYSIS | | | |
| --- | --- | --- | --- |
| Calculated for C$_{15}$H$_{13}$N$_3$O.C$_4$H$_4$O$_4$ | 62.13% C | 4.63% H | 11.44% N |
| Found | 62.30% C | 4.74% H | 11.49% N |

EXAMPLE 24

1-(Methyl-4-quinolinamino)-1H-pyrrole-3-carboxaldehyde maleate

To dry DMF (18.25 ml) at ice bath temperature was added phosphorous oxychloride (24.48 ml), dropwise. This mixture was stirred for five minutes and then a solution of N-methyl-N-(1H-pyrrol-1-yl)-4-quinolinamine (27 g) in 250 ml of DCE was added rapidly to the mixture. The reaction mixture was then stirred at room temperature for one hour and then heated to 80° C. and stirred for three hours.

The mixture was cooled, treated with an aqueous solution of NaC$_2$H$_3$O$_2$.3H$_2$O (45 g) and then stirred for fifteen minutes at 70° C. This mixture was then cooled and poured into iced water, which was treated with 50% NaOH aqueous solution (90 ml) and then extracted with DCM (4×). The organics were combined, washed with water and dried (sat. NaCl, anh. MgSO$_4$).

After filtration, the solvent was evaporated to yield an oil (39.3 g) which was eluted with hexane/THF (1:2) on silica gel columns via HPLC. The desired fractions were concentrated to yield a solid (27.4 g) which was eluted with 20% hexane/ether on a silica gel column via flash chromatography. The desired fractions were concentrated to yield an oil (1.9 g). This material was dissolved in ethyl acetate and acidified with maleic acid. The resulting precipitate was collected to yield 1.4 g solid, m.p. 139°–141° C.

| ANALYSIS | | | |
|---|---|---|---|
| Calculated for C$_{15}$H$_{13}$N$_3$O.C$_4$H$_4$O$_4$ | 62.13% C | 4.63% H | 11.44% N |
| Found | 62.26% C | 4.60% H | 11.38% N |

EXAMPLE 25

1-[(7-Chloro-4-quinolinyl)methylamino]-1H-pyrrole-2-carboxaldehyde maleate

To ice cold DMF (22 ml) was added dropwise POCl$_3$ (30 ml) over a period of fifteen minutes. The mixture was stirred at ambient temperature for fifteen minutes, then a solution of 7-chloro-N-methyl-N-(1H-pyrrol-1-yl)-4-quinolinamine (26 g) in 200 ml DCE was added in ten minutes.

The mixture was stirred at 90° C. for two hours, and thereafter it was cooled, then a solution of NaOCOCH$_3$.3H$_2$O (90 g) in 200 ml water was added, and the mixture was heated at 80° C. for fifteen minutes.

After cooling, the mixture was poured into 200 ml ice water, stirred for five minutes, then basified to pH 12 with 80 ml 50% NaOH solution. The DCE layer was combined with the ethyl acetate extract of the aqueous layer, washed with water and dried (saturated NaCl, anhydrous MgSO$_4$).

After filtration, the solvent was evaporated to yield 30 g of an oil, which was eluted on a silica gel column with ethyl acetate via HPLC. The desired fractions were combined and concentrated to yield an oil, which solidified to a pale yellow solid, 23.6 g, m.p. 99°–100° C.

A 3.0 g sample of this solid was dissolved in ether, the pH adjusted to 1 with maleic acid, and the resulting precipitate collected and dried to give 4.8 g, dec at 165° C. This material was recrystallized from ethanol/ether (1:1) to give 3.4 g crystals, dec. at 168° C.

| ANALYSIS: | | | |
|---|---|---|---|
| Calculated for C$_{15}$H$_{12}$ClN$_3$O.C$_4$H$_4$O$_4$: | 56.79% C | 4.01% H | 10.46% N |
| Found: | 56.86% C | 3.99% H | 10.53% N |

EXAMPLE 26

1-[(7-Chloro-4-quinolinyl)methylamino]-1H-pyrrole-3-carboxaldehyde maleate

To ice cold DMF (22 ml) was added dropwise POCl$_3$ (30 ml) over a period of fifteen minutes. The mixture was stirred at ambient temperature for fifteen minutes, then a solution of 7-chloro-N-methyl-N-(1H-pyrrol-1-yl)-4-quinolinamine (26 g) in 200 ml DCE was added in ten minutes.

After stirring at 90° C. for two hours, the mixture was cooled, then a solution of NaOCOCH$_3$.3H$_2$O (90 g) in 200 ml water was added, and the mixture was heated at 80° C. for fifteen minutes.

After cooling, the mixture was poured into 200 ml ice-water, stirred for five minutes, then basified to pH 12 with 80 ml 50% NaOH solution. The DCE layer was combined with the ethyl acetate extract of the aqueous layer, washed with water and dried (saturated NaCl, anhydrous MgSO$_4$).

After filtration, the solvents were evaporated to yield 30 g of an oil, which was eluted on a silica gel column with ethyl acetate via HPLC. The desired fractions were combined and concentrated to yield an oil, which solidified on cooling to 3.4 g solid, m.p. 129°–131° C.

This material was dissolved in ethanol, and to it was added an ethanolic solution of maleic acid (1.3 g). Upon dilution with ether, a precipitate formed which was collected and dried to give 2.3 g of a solid, dec. at 152° C. This material was recrystallized from ethanol/ether (1:10) to give 2.1 g of a solid, dec. at 151° C.

| ANALYSIS: | | | |
|---|---|---|---|
| Calculated for C$_{15}$H$_{12}$ClN$_3$O. C$_4$H$_4$O$_4$: | 56.79% C | 4.01% H | 10.46% N |
| Found: | 56.75% C | 4.02% H | 10.42% N |

EXAMPLE 27

1-[(7-Chloro-4-quinolinyl)propylamino]-1H-pyrrole-2-carboxaldehyde maleate

To DMF (13.7 ml) at ice bath temperature was added POCl$_3$ (18.36 ml) dropwise, and after the addition was complete this mixture was stirred for five minutes at ice bath temperature. Then a solution of 7-chloro-N-propyl-N-(1H-pyrrol-1-yl)-4-quinolinamine (25.5 g) in 200 ml of DCE was added dropwise over twenty minutes. After the addition was complete, the reaction mixture was heated to 80° C. and stirred vigorously for six hours.

The mixture was then cooled and treated with a solution of NaC$_2$H$_3$O$_2$.3H$_2$O (45 g) in 200 ml of water. After stirring for ten minutes, the mixture was basified with K$_2$CO$_3$. The basified aqueous mixture was then extracted with DCM, and the organics were combined, washed with water and dried (sat. NaCl, and MgSO$_4$).

After filtration, the solvent was evaporated to yield an oil (28 g), which was eluted with 20% hexanes/ether on silica gel columns via HPLC. The desired fractions were concentrated to yield an oil (8.34 g). Of this, 3.0 g was dissolved in methanol and acidified with maleic acid.

The resulting precipitate was collected to yield a solid (3.23 g), which was recrystalized from methanol/ether (5:1). The resulting crystals were collected to yield 2.35 g of a solid, m.p. 180°–181° C.

| ANALYSIS: | | | |
|---|---|---|---|
| Calculated for C$_{17}$H$_{16}$ClN$_3$O. C$_4$H$_4$O$_4$: | 58.67% C | 4.66% H | 9.78% N |
| Found: | 58.58% C | 4.76% H | 9.78% N |

EXAMPLE 28

1-[(7-Chloro-4-quinolinyl)propylamino]-1H-pyrrole-3-carboxaldehyde maleate

To DMF (13.7 ml) at ice bath temperature was added $POCl_3$ (18.36 ml) dropwise, and after the addition was complete, this mixture was stirred for five minutes at ice bath temperature. Then a solution of 7-chloro-N-propyl-N-(1H-pyrrol-1-yl)-4-quinolinamine (25.5 g) in 200 ml of DCE was added dropwise over twenty minutes. After the addition was complete, the reaction mixture was heated to 80° C. and stirred vigorously for six hours.

The mixture was then cooled and treated with a solution of $NaC_2H_3O_2.3H_2O$ (45 g) in 200 ml of water. After stirring for ten minutes, the mixture was basified with $K_2CO_3$. The basified aqueous mixture was then extracted with DCM, and the organics were combined, washed with water and dried (sat. NaCl, and $MgSO_4$).

After filtration, the solvent was evaporated to yield an oil (28 g), which was eluted with 20% hexanes/ether on silica gel columns via HPLC. The desired fractions were concentrated to yield an oil (6.0 g). This material was dissolved in isopropanol and acidified with maleic acid. The resulting precipitate was collected to yield a solid (6.5 g), which was recrystallized from ethyl acetate/methanol (5:1). The resulting crystals were collected to yield 4.06 g solid, m.p. 172°–174° C.

| ANALYSIS: | | | |
|---|---|---|---|
| Calculated for $C_{17}H_{16}ClN_3O$. $C_4H_4O_4$: | 58.67% C | 4.66% H | 9.78% N |
| Found: | 58.41% C | 4.65% H | 9.68% N |

EXAMPLE 29

N-Methyl-N-(2-ethenyl-1H-pyrrol-1-yl)-4-quinolinamine maleate

To a stirred mixture of methyltriphenylphosphonium bromide (14.29 g) in 200 ml of ether at ice bath temperature was added potassium t-butoxide and this mixture was stirred at ice bath temperature for ten minutes. Then a solution of 1-[(methyl)-4-quinolinylamino]-1H-pyrrole-2-carboxaldehyde (8.0 g) in 100 ml ether was added. This mixture was stirred for four hours at ice bath temperature.

The mixture was poured into iced water and extracted with ethyl acetate. The organic layer was washed with water and dried (sat. NaCl, anhy. $MgSO_4$).

After filtration, the solvent was evaporated to yield an oil, which solidified on standing (20.66 g). This was eluted with 10% ethyl acetate/DCM on a silica gel column via HPLC. The desired fractions were concentrated to yield an oil, which solidified on standing (10.45 g). Of this material 5.5 g was dissolved in ethyl acetate and acidified with maleic acid. The resulting precipitate was collected to yield a solid (4.3 g), which was recrystallized from ethyl acetate/methanol (10:1). The resulting crystals were collected to yield 4.0 solid, m.p. 146°–148° C.

| ANALYSIS: | | | |
|---|---|---|---|
| Calculated for $C_{16}H_{15}N_3O$. $C_4H_4O_4$: | 65.75% C | 5.21% H | 11.51% N |
| Found: | 65.84% C | 5.12% H | 11.45% N |

EXAMPLE 30

7-Chloro-N-(2-ethenyl-1H-pyrrol-1-yl)-N-methyl-4-quinolinamine maleate

To a cold solution of methyltriphenylphosphonium bromide (14.3 g) in 100 ml of ether, was added potassium t-butoxide (4.4 g) portionwise in fifteen minutes. The resultant solution was stirred at 0° C. for an additional fifteen minutes.

To this cold solution was added a solution of 1-[7-chloro-4-quinolinyl)methylamino]-1H-pyrrole-2-carboxaldehyde in 400 ml ether in about twenty minutes and stirring was continued at 5° C. for one hour.

The mixture was poured into one liter of water and stirred for five minutes, the ether solution collected, and the aqueous layer extracted with ether. The combined ether layers were washed with water and dried (saturated NaCl, anhydrous $MgSO_4$).

After filtration, the solvent was evaporated to yield 19 g of an oil, which was eluted on a silica gel column with ethyl acetate/DCM (1:1) via HPLC. The desired fractions were combined and concentrated to yield 13 g of an oil.

This oil was dissolved in ether and acidified to pH 1 with ethereal maleic acid. The resultant precipitate was collected, washed with ether and dried to give 9.6 g of a solid, dec. at 155° C. A 4.2 g portion of this material was recrystallized from ethanol/ether (1:10) to give 2.7 g solid, dec. at 160° C.

| ANALYSIS: | | | |
|---|---|---|---|
| Calculated for $C_{16}H_{14}ClN_3$. $C_4H_4O_4$: | 60.08% C | 4.54% H | 10.51% N |
| Found: | 60.00% C | 4.58% H | 10.42% N |

EXAMPLE 31

7-Chloro-N-propyl-N-(2-ethenyl-1H-pyrrol-1-yl)-4-quinolinamine

To a stirred mixture of methyltriphenylphosphonium bromide (7.14 g) and 150 ml of diethyl ether at ice bath temperature was added n-butyllithium (12 ml, 0.020 mole) dropwise. After the addition was complete, the mixture was stirred for fifteen minutes at ice bath temperature and then a solution of 1-[(7-chloro-4-quinolinyl)propylamino]-1H-pyrrole-2-carboxaldehyde (4.6 g) in 80 ml of ether was added dropwise. The mixture was stirred for four hours at ice bath temperature.

The mixture was poured into water and extracted with ethyl acetate. The organic layer was washed with water and dried (sat. NaCl, and $MgSO_4$).

After filtration, the solvent was evaporated to yield an oil (5.6 g), which was eluted with 10% ethyl acetate/DCM on a silica gel column via HPLC. The desired fractions were concentrated to yield an oil, which solidified on standing, 2.45 g, m.p. 102°–105° C.

| ANALYSIS: | | | |
|---|---|---|---|
| Calculated for $C_{18}H_{18}ClN_3$: | 69.34% C | 5.78% H | 13.48% N |

| ANALYSIS: | | | |
|---|---|---|---|
| Found: | 69.03% C | 5.75% H | 13.28% N |

EXAMPLE 32

3-[1-(Methyl-4-quinolinyl)amino-1H-pyrrol-2-yl]-2-propenoic acid, ethyl ester maleate To a stirred solution of triethyl phosphonoacetate (4.5 g) in 35 ml of 1,2-dimethoxyethane (DME) at ice bath temperature was added portionwise a suspension of NaH (0.8 g of 60% NaH dispersion in oil). After the addition was complete, the mixture was stirred at room temperature for one hour. Then a solution of 1-[(methyl)-4-quinolinylamino]-1H-pyrrole-2-carboxaldehyde (3.3 g) in 50 ml DME was added dropwise, and thereafter the mixture was heated to 90° and stirred for two hours.

The reaction mixture was poured into water and extracted with ethyl acetate. The organic layer was washed with water and dried (sat. NaCl, and $MgSO_4$).

After filtration, the solvent was evaporated to yield an oil (5.2 g), which was eluted with 10% ethyl acetate/DCM on a silica gel column via HPLC. The desired fractions were concentrated to yield an oil (4.6 g), which was dissolved in ethanol and acidified with maleic acid. The resulting precipitate was collected to yield a solid (4.0 g), which was recrystallized from ethanol to yield 3.57 g solid, m.p. 172°–174° C.

| ANALYSIS: | | | |
|---|---|---|---|
| Calculated for $C_{19}H_{19}N_3O_2 \cdot C_4H_4O_4$: | 63.16% C | 5.26% H | 9.61% N |
| Found: | 62.90% C | 5.21% H | 9.63% N |

EXAMPLE 33

3-[1-[(7-Chloro-4-quinolinyl)methylamino]-1H-pyrrol-2-yl]-2-propenoic acid, ethyl ester maleate To a cold solution of triethyl phosphonoacetate (4.5 g) in 35 ml DME, was added portionwise in five minutes a suspension of NaH (0.8 g of 60% NaH dispersion in oil). After stirring at ambient temperature for one hour, a solution of 1-[(7-chloro-4-quinolinyl)methylamino]-1H-pyrrole-2-carboxaldehyde (4.0 g) in 25 ml DME was added in five minutes.

After stirring at 90° C. for two hours, the mixture was cooled, poured into 200 ml water, stirred for five minutes and extracted with ethyl acetate/DCM. The organic layer was washed with water and dried (sat. NaCl, anhy. $MgSO_4$).

After filtration, the solvent was evaporated to yield 7.0 g solid m.p. 140°–145° C., which was eluted on a silica gel column with ethyl acetate/DCM (1:5) via HPLC. The desired fractions were combined and concentrated to 5.2 g solid, m.p. 150°–155° C., which was triturated with ether to give 4.2 g solid, m.p. 157°–159° C.

This material was dissolved in hot ethyl acetate and the solution was acidified to pH 1 with ethereal maleic acid to give 5.0 g solid, dec. at 165°–168° C., which was recrystallized from ethanol/ether (1:4) to give 3.4 g crystals, dec. at 169° C.

| ANALYSIS: | | | |
|---|---|---|---|
| Calculated for $C_{19}H_{18}ClN_3O_2 \cdot C_4H_4O_4$: | 58.54% C | 4.70% H | 8.90% N |
| Found: | 58.36% C | 4.59% H | 8.87% N |

EXAMPLE 34

N-Methyl-N-(2-ethyl-1H-pyrrol-1-yl)-4-quinolinamine maleate

To a hydrogenation bottle were charged a slurry of 10% Pd/C (1.0 g) in 5 ml of absolute ethanol and a solution of N-methyl-N-(2-ethenyl-1H-pyrrol-1-yl)-4-quinolinamine (4.0 g) in 245 ml of absolute ethanol. The bottle was pressurized with $H_2$ to 50 psi and shaken on a Parr apparatus for 45 minutes.

The mixture was filtered through celite, and the filtrate concentrated to yield an oil (4.0 g). This material was dissolved in ethyl acetate and acidified with maleic acid. The resulting precipitate was collected to yield 2.3 g solid, m.p. 131°–133° C.

| ANALYSIS: | | | |
|---|---|---|---|
| Calculated for $C_{16}H_{17}N_3 \cdot C_4H_4O_4$: | 65.40% C | 5.72% H | 11.44% N |
| Found: | 65.36% C | 5.66% H | 11.52% N |

EXAMPLE 35

7-Chloro-N-(2-ethyl-1H-pyrrol-1-yl)-N-methyl-4-quinolinamine maleate

To a suspension of 5% Pt/C (1.0 g) in 25 ml ethanol was added a solution of 7-chloro-N-(2-ethenyl-1H-pyrrol-1-yl)-N-methyl-4-quinolinamine (3.9 g) in 200 ml ethanol. The mixture was pressured with $H_2$ to 50 psi and shaken at ambient temperature for five hours.

The mixture was filtered, and the solvent evaporated to yield 3.0 g solid, m.p. 113°–115° C. This material was dissolved in ether and the solution was acidified to pH 1 with ethereal maleic acid. The resulting precipitate was collected and dried to give 4.0 g, m.p. 145°–147° C., which was recrystallized from ethanol/ether (1:20) to give 3.3. g, m.p. 145°–147° C.

| ANALYSIS: | | | |
|---|---|---|---|
| Calculated for $C_{16}H_{16}ClN_3 \cdot C_4H_4O_4$: | 59.78% C | 5.02% H | 10.46% N |
| Found: | 59.75% C | 4.91% H | 10.44% N |

EXAMPLE 36

7-Chloro-N-(2-diethylaminomethyl-1H-pyrrol-1-yl)-4-quinolinamine

To a solution of 7-chloro-N-(1H-pyrrol-1-yl)-quinolinamine (6.0 g) in 120 ml of absolute ethanol was added a solution of diethylamine hydrochloride (2.9 g) and formaldehyde (37 wt % in water, 21.08 ml) dropwise. The solution was heated to 60° C. and stirred for two hours. The mixture was poured into water and basified with $Na_2CO_3$ (aq) and extracted with ethyl acetate, and the organic layer was washed with water and dried (sat. NaCl, anhy. $MgSO_4$).

After filtration, the solvent was evaporated to yield an oil (11.5 g), which was eluted with ethyl acetate on a silica gel column via flash chromatography. The desired fractions were concentrated to yield a solid (3.04 g). This material was recrystallized from hexane/ether (1:1) to yield 1.84 g solid, m.p. 151°–152° C.

| ANALYSIS: | | | |
|---|---|---|---|
| Calculated for $C_{18}H_{21}ClN_4$: | 65.75% C | 6.39% H | 17.05% N |
| Found: | 65.62% C | 6.38% H | 17.06% N |

EXAMPLE 37

N-(2-Diethylaminomethyl-1H-pyrrol-1-yl)-N-methyl-7-trifluoromethyl-4-quinolinamine To a mixture of N-methyl-N-(1H-pyrrol-1-yl)-7-trifluoromethyl-4-quinolinamine (9.0 g) and 200 ml of 1,4-dioxane were added paraformaldehyde (4 g), diethylamine hydrochloride (4.5 g) and CuCl (0.2 g) and this mixture was heated to 80° C. and stirred for five hours. The mixture was cooled and diluted with ethyl acetate, and the organic layer was washed with water and dried (sat. NaCl, anhy. MgSO4).

After filtration, the solvent was evaporated to yield an oil (11.0 g), which was eluted with 50% ethyl acetate/DCM on a silica gel column via HPLC. The desired fractions were concentrated to yield an oil (2.8 g). This oil was dissolved in ethanol and acidified with ethereal/HCl. The resulting precipitate was collected to yield a solid, 2.4 g (m.p. 225°–227° C.), which was recrystallized from methanol/ether (1:5) to yield a solid (1.2 g). This material was then converted back to the free base to yield an oil which solidified on standing, 1.1. g, m.p. 64°–66° C.

| ANALYSIS: | | | |
|---|---|---|---|
| Calculated for $C_{20}H_{23}F_3N_4$: | 63.82% C | 6.16% H | 14.88% N |
| Found: | 63.72% C | 6.47% H | 14.80% N |

EXAMPLE 38

7-Chloro-N-[2-(1-piperidinyl)methyl-1H-pyrrol-1-yl]-4-quinolinamine

To a solution of 7-chloro-N-(1H-pyrrol-1-yl)-4-quinolinamine (5.0 g) in 75 ml ethanol were added formaldehyde (37% aqueous solution, 5 ml) and piperidine hydrochloride (2.1 g).

After stirring at 70° C. for three hours, the mixture was poured into 200 ml water, the pH was adjusted to 10 with a Na2CO3 solution and the mixture was extracted with ethyl acetate. The organic layer was washed with water and dried (sat. NaCl, anhy. MgSO4).

After filtration, the solvent was evaporated to yield about 8 g of oil, which was eluted on a silica gel column with ethyl acetate via HPLC. The desired fractions were concentrated to 1.5 g solid, m.p. 155°–157° C.

| ANALYSIS: | | | |
|---|---|---|---|
| Calculated for $C_{19}H_{21}ClN_4$: | 66.95% C | 6.21% H | 16.44% N |
| Found: | 66.67% C | 6.20% H | 16.25% N |

EXAMPLE 39

7-Chloro-N-[4-[4-methylpiperazin-1-yl]-2-butynyl]-N-(1H-pyrrol-1-yl)-4-quinolinamine To a solution of 7-chloro-N-(2-propynyl)-N-(1H-pyrrol-1-yl)-4-quinolinamine (8.0 g) in 150 ml of 1,4-dioxane were added N-methylpiperazine (3.11 g), paraformaldehyde (4 g) and CuCl (0.2 g), and this mixture was heated to 80° C. and stirred for four hours. The mixture was cooled, diluted with ethyl acetate, washed with water and dried (sat NaCl, anhy. MgSO4).

After filtration, the solvent was evaporated to yield an oil (14.2 g), which was eluted with 7.5% methanol/DCM on a silica gel column via HPLC. The desired fractions were concentrated to yield an oil (10 g), which was eluted again with 5% methanol/DCM on a silica gel column via HPLC. The desired fractions were concentrated to yield an oil which solidified on standing, 6.7 g, m.p. 85°–88° C.

| ANALYSIS: | | | |
|---|---|---|---|
| Calculated for $C_{22}H_{24}ClN_5$: | 67.09% C | 6.10% H | 17.79% N |
| Found: | 66.73% C | 6.16% H | 17.63% N |

EXAMPLE 40

7-Chloro-N-[4-[4-(2-methoxyphenyl)piperazin-1-yl]-2-butynyl]-N-(1H-pyrrol-1-yl)-4-quinolinamine To 1,4-dioxane (150 ml) were added 7-chloro-N-(2-propynyl)-N-(1H-pyrrol-1-yl)-4-quinolinamine (6.0 g), 1-(2-methoxyphenyl)piperazine (4.42 g), paraformaldehyde (4 g) and CuCl (0.2 g) and this mixture was heated to 80° C. and stirred for six hours. After cooling, the mixture was diluted with ethyl acetate and filtered, and the filtrate was eluted with ethyl acetate on a silica gel column via HPLC. The desired fractions were concentrated to yield a solid (5.4 g). Of this material, 3.0 g was recrystallized from isopropyl ether/methanol (5:1), and the resulting crystals were collected to yield 2.2 g solid, m.p. 120°–122° C.

| ANALYSIS: | | | |
|---|---|---|---|
| Calculated for $C_{28}H_{28}ClN_5O$: | 69.21% C | 5.77% H | 14.42% N |
| Found: | 69.29% C | 5.81% H | 14.41% N |

We claim:

1. A compound of the formula

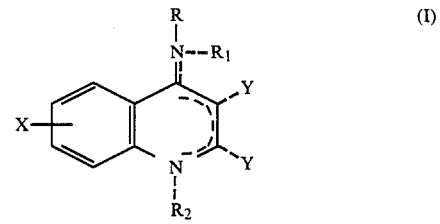

where
—R is

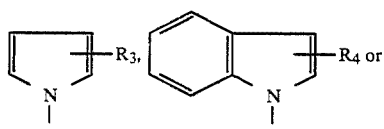

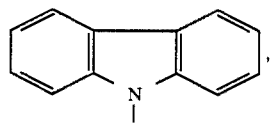

—R₃ and R₄ being independently —H, loweralkyl, —CHO, —CH=CH₂, —CH=CH—loweralkyl, —CH=CHCO₂C₂H₅, —CH₂N(C₂H₅)₂ or

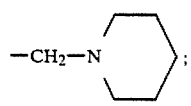

—R₁ when existent is —H, loweralkyl, —CH₂C≡CH,

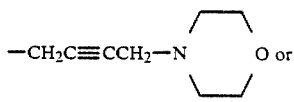

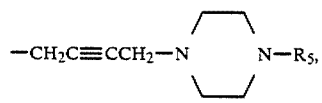

R₅ being methyl or phenyl optionally mono-substituted with loweralkyl or loweralkoxy;
—R₂ when existent is loweralkyl or —CH₂CH=CH;
—X is —H, loweralkyl, loweralkoxy, halogen or trifluoromethyl; and the two —Y groups when existent are both —H, or combine to constitute —(CH₂)₄—;
or a pharmaceutically acceptable acid addition salt thereof.

2. The compound as defined in claim 1, where both —Y are —H.

3. The compound as defined in claim 2, where —R is

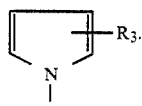

4. The compound as defined in claim 2, where —R is

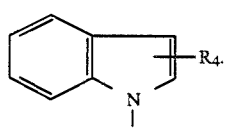

5. The compound as defined in claim 2, where —R is

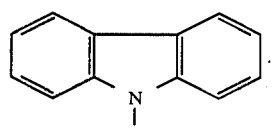

6. The compound as defined in claim 1, where the two —Y groups together constitute —(CH₂)₄—.

7. The compound as defined in claim 6, where —R is

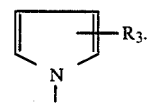

8. The compound as defined in claim 6, where —R is

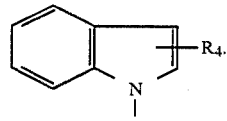

9. The compound as defined in claim 6, where —R is

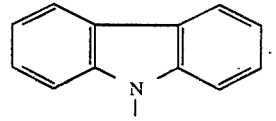

10. The compound as defined in claim 1, where both —Y groups are absent.

11. The compound as defined in claim 10, where —R is

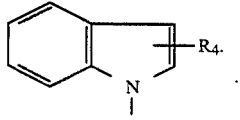

12. The compound as defined in claim 10, where —R is

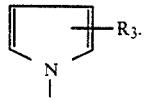

13. The compound as defined in claim 10, where —R is

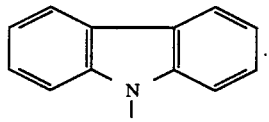

14. The compound as defined in claim 1, which is N-(1H-pyrrol-1-yl)-4-quinolinamine.

15. The compound as defined in claim 1, which is 7-chloro-N-(1H-pyrrol-1-yl)-4-quinolinamine.

16. The compound as defined in claim 1, which is N-(1H-pyrrol-1-yl)-7-trifluoromethyl-4-quinolinamine.

17. The compound as defined in claim 1, which is N-methyl-N-(1H-pyrrol-1-yl)-4-quinolinamine.

18. The compound as defined in claim 1, which is 7-chloro-N-methyl-N-(1H-pyrrol-1-yl)-4-quinolinamine.

19. The compound as defined in claim 1, which is N-(1H-pyrrol-1-yl)-7-trifluoromethyl-4-quinolinamine.

20. The compound as defined in claim 1, which is 7-chloro-N-propyl-N-(1H-pyrrol-1-yl)-4-quinolinamine.

21. The compound as defined in claim 1, which is N-(1H-indol-1-yl)-4-quinolinamine.

22. The compound as defined in claim 1, which is N-(3-methyl-1H-indol-1-yl)-4-quinolinamine.

23. The compound as defined in claim 1, which is 7-chloro-N-(1H-indol-1-yl)-N-propyl-4-quinolinamine.

24. The compound as defined in claim 1, which is N-(1H-pyrrol-1-yl)-1,2,3,4-tetrahydro-9-acridinamine.

25. The compound as defined in claim 1, which is N-(1H-indol-1-yl)-1,2,3,4-tetrahydro-9-acridinamine.

26. The compound as defined in claim 1, which is N-(3-methyl-1H-indol-1-yl)-1,2,3,4-tetrahydro-9-acridinamine.

27. The compound as defined in claim 1, which is N-(4-quinolinyl)-9H-carbazol-9-amine.

28. The compound as defined in claim 1, which is N-(2-methyl-1H-indol-1-yl)-1,2,3,4-tetrahydro-9-acridinamine.

29. The compound as defined in claim 1, which is N-propyl-N-(1H-pyrrol-1-yl)-4-quinolinamine.

30. The compound as defined in claim 1, which is 1-propyl-N-(1H-pyrrol-1-yl)-4(1H)-quinolinimine.

31. The compound as defined in claim 1, which is 7-chloro-N-(2-propynyl)-N-(1H-pyrrol-1-yl)-4-quinolinamine.

32. The compound as defined in claim 1, which is 7-chloro-1-(2-propynyl)-N-(1H-pyrrol-1-yl)-4(1H)-quinolinimine.

33. The compound as defined in claim 1, which is N-(3-methyl-1H-indol-1-yl)-N-propyl-1,2,3,4-tetrahydro-9-acridinamine.

34. The compound as defined in claim 1, which is N-propyl-N-(4-quinolinyl)-9H-carbazol-9-amine.

35. The compound as defined in claim 1, which is N-(9H-carbazol-9-yl)-1-propyl-4(1H)-quinolinimine.

36. The compound as defined in claim 1, which is 1-(methyl-4-quinolinylamino)-1H-pyrrole-2-carboxaldehyde.

37. The compound as defined in claim 1, which is 1-(methyl-4-quinolinylamino)-1H-pyrrole-3-carboxaldehyde.

38. The compound as defined in claim 1, which is 1-[(7-chloro-4-quinolinyl)-methylamino]-1H-pyrrole-2-carboxaldehyde.

39. The compound as defined in claim 1, which is 1-[(7-chloro-4-quinolinyl)-methylamino]-1H-pyrrole-3-carboxaldehyde.

40. The compound as defined in claim 1, which is 1-[(7-chloro-4-quinolinyl)-propylamino]-1H-pyrrole-2-carboxaldehyde.

41. The compound as defined in claim 1, which is 1-[(7-chloro-4-quinolinyl)-propylamino]-1H-pyrrole-3-carboxaldehyde.

42. The compound as defined in claim 1, which is N-methyl-N-(2-ethenyl-1H-pyrrol-1-yl)-4-quinolinamine.

43. The compound as defined in claim 1, which is 7-chloro-N-(2-ethenyl-1H-pyrrol-1-yl)-N-methyl-4-quinolinamine.

44. The compound as defined in claim 1, which is 7-chloro-N-propyl-N-(2-ethenyl-1H-pyrrol-1-yl)-4-quinolinamine.

45. The compound as defined in claim 1, which is 3-[1-(methyl-4-quinolinylamino)-1H-pyrrol-2-yl]-2-propenoic acid, ethyl ester.

46. The compound as defined in claim 1, which is 3-[1-[(7-chloro-4-quinolinyl)methylamino]-1H-pyrrol-2-yl]-2-propenoic acid, ethyl ester.

47. The compound as defined in claim 1, which is N-methyl-N-(2-ethyl-1H-pyrrol-1-yl)-4-quinolinamine.

48. The compound as defined in claim 1, which is 7-chloro-N-(2-ethyl-1H-pyrrol-1-yl)-N-methyl-4-quinolinamine.

49. The compound as defined in claim 1, which is 7-chloro-N-(2-diethylaminomethyl-1H-pyrrol-1H-pyrrol-1-yl)-4-quinolinamine.

50. The compound as defined in claim 1, which is N-(2-diethylaminomethyl-1H-pyrrol-1-yl)-N-methyl-7-trifluoromethyl-4-quinolinamine.

51. The compound as defined in claim 1, which is 7-chloro-N-[2-(1-piperidinyl)methyl-1H-pyrrol-1-yl]-4-quinolinamine.

52. The compound as defined in claim 1, which is 7-chloro-N-[4-[4-methylpiperazin-1-yl]-2-butynyl]-N-(1H-pyrrol-1-yl)-4-quinolinamine.

53. The compound as defined in claim 1, which is 7-chloro-N-[4-[4-(2-methoxyphenyl)piperazin-1-yl]-2-butynyl]-N-(1H-pyrrol-1-yl)-4-quinolinamine.

54. A pharmaceutical composition comprising a compound as defined in claim 1 in an amount effective for alleviating pain or a memory dysfunction characterized by decreased cholinergic function, and a suitable carrier therefor.

55. A method of treating a patient in need of relief from pain which comprises administering to such a patient an effective amount of a compound as defined in claim 1.

56. A method of treating a patient in need of relief from a memory dysfunction characterized by decreased cholinergic function which comprises administering to such a patient an effective amount of a compound as defined in claim 1.

* * * * *